US010792435B2

(12) United States Patent
Davis et al.

(10) Patent No.: US 10,792,435 B2
(45) Date of Patent: Oct. 6, 2020

(54) INJECTOR WITH READY TO USE INDICATOR

(71) Applicant: West Pharmaceutical Services, Inc., Exton, PA (US)

(72) Inventors: Tommy Gene Davis, Athens, TX (US); Brian Klueppel, Tyler, TX (US); Paul Benson, Tyler, TX (US); Anthony G. Esposito, Fountain Hills, AZ (US); Jason Choi, Gilbert, AZ (US)

(73) Assignee: West Pharmaceutical Services, Inc., Exton, PA (US)

( * ) Notice: Subject to any disclaimer, the term of this patent is extended or adjusted under 35 U.S.C. 154(b) by 0 days.

(21) Appl. No.: 16/500,878

(22) PCT Filed: Apr. 6, 2018

(86) PCT No.: PCT/US2018/026556
§ 371 (c)(1),
(2) Date: Oct. 4, 2019

(87) PCT Pub. No.: WO2018/187744
PCT Pub. Date: Oct. 11, 2018

(65) Prior Publication Data
US 2020/0030544 A1 Jan. 30, 2020

Related U.S. Application Data

(60) Provisional application No. 62/482,496, filed on Apr. 6, 2017.

(51) Int. Cl.
*A61M 5/315* (2006.01)
*A61M 5/31* (2006.01)
*A61M 5/44* (2006.01)

(52) U.S. Cl.
CPC ........... *A61M 5/31566* (2013.01); *A61M 5/44* (2013.01); *A61M 2005/3125* (2013.01);
(Continued)

(58) Field of Classification Search
CPC ........ A61M 5/31566; A61M 2205/581; A61M 2205/582; A61M 2205/583; A61M 2205/3606; A61M 2005/3125
See application file for complete search history.

(56) References Cited

U.S. PATENT DOCUMENTS 6,810,350 B2  10/2004  Blakley
8,226,610 B2   7/2012  Edwards et al.
(Continued)

FOREIGN PATENT DOCUMENTS

EP    3100754 A1   12/2016
JP    2014516667 A  7/2014

OTHER PUBLICATIONS

Int'l Search Report and Written Opinion dated Jul. 12, 2018 in Int'l Application No. PCT/US2018/026556.
(Continued)

*Primary Examiner* — Jason E Flick
*Assistant Examiner* — Tasnim Mehjabin Ahmed
(74) *Attorney, Agent, or Firm* — Panitch Schwarze Belisario & Nadel LLP

(57) ABSTRACT

An injection system, including an injector having a dispensing mechanism configured to dispense a medicament, and a ready-to-use indicator. The ready-to-use indicator includes a controller configured to interact with the ready-to-use indicator and an audio and/or visual indicator, a temperature sensor, and a temperature analog having similar thermodynamic properties of the medicament. The temperature sensor is configured to detect a temperature of the temperature analog which represents the dynamic temperature of medi-
(Continued)

cament as the medicament is heated or cooled. The temperature sensor is configured to communicate the detected temperature to the controller and to alert the controller when a preset temperature is reached. The ready-to-use indicator is configured to alert a user when the preset temperature is reached, signifying the medicament is thermally ready to be delivered by the dispensing mechanism. The audio and/or visual indicator is configured to display indicate one or more notifications to the user.

18 Claims, 15 Drawing Sheets

(52) U.S. Cl.
CPC ............... *A61M 2205/3368* (2013.01); *A61M 2205/3606* (2013.01); *A61M 2205/502* (2013.01); *A61M 2205/581* (2013.01); *A61M 2205/582* (2013.01); *A61M 2205/583* (2013.01); *A61M 2205/587* (2013.01); *A61M 2205/8206* (2013.01)

(56) References Cited

U.S. PATENT DOCUMENTS

| | | | |
|---|---|---|---|
| 8,827,964 B2 | 9/2014 | Boyd et al. | |
| 9,181,008 B2 | 11/2015 | Milan | |
| 9,278,177 B2 | 3/2016 | Edwards et al. | |
| 9,470,587 B1 | 10/2016 | Greene | |
| 2002/0188419 A1 | 12/2002 | Slate et al. | |
| 2007/0239116 A1 | 10/2007 | Follman et al. | |
| 2008/0312604 A1* | 12/2008 | Boesen | A61M 5/31568 604/207 |
| 2009/0024112 A1 | 1/2009 | Edwards et al. | |
| 2009/0030366 A1* | 1/2009 | Hochman | A61M 5/20 604/67 |
| 2010/0211005 A1* | 8/2010 | Edwards | A61M 15/008 604/82 |
| 2014/0155827 A1 | 6/2014 | Ostrander et al. | |
| 2015/0011965 A1 | 1/2015 | Cabiri | |
| 2015/0061389 A1 | 3/2015 | Song et al. | |
| 2015/0080810 A1 | 3/2015 | Henderson et al. | |
| 2017/0224934 A1 | 8/2017 | Shultz et al. | |
| 2017/0348478 A1 | 12/2017 | Tobescu | |

OTHER PUBLICATIONS

International Preliminary Report on Patentability dated Oct. 8, 2019 in Int'l Application No. PCT/US2018/026556.

Office Action dated Mar. 17, 2020 in JP Application No. 2019-554804.

Extended European Search Report dated Aug. 5, 2020 in European Application No. 18780556.9.

* cited by examiner

INJECTOR WITH READY TO USE INDICATOR

CROSS-REFERENCE TO RELATED APPLICATIONS

This application is a section 371 of International Application No. PCT/US18/026556, filed Apr. 6, 2018, which was published on Oct. 11, 2018 under International Publication No. WO 2018/187744 A1, and which claims priority to U.S. Provisional Patent Application No. 62/482,496, filed Apr. 6, 2017, the contents of each of which are incorporated herein by reference in their entirety.

BACKGROUND

In many instances of medication delivery, the medicament must be stored in a cold environment in order to prevent spoilage. However, injection of cold medication may be painful or uncomfortable to a patient. Moreover, certain medicaments must be delivered at certain temperatures in order to maximize efficacy. In order to determine whether the medicament in a particular delivery device has reached proper temperature after being removed from cold storage, a ready-to-use indicator system may be advantageous.

SUMMARY

Embodiments may provide an injection system, which may comprise an injector, which may further comprise a dispensing mechanism configured to dispense a medicament; a ready-to-use indicator that may further comprise a controller configured to interact with the ready-to-use indicator and an audio and/or visual indicator; a temperature sensor; and a temperature analog having similar thermodynamic properties of the medicament; wherein the temperature sensor is configured to detect a temperature of the temperature analog which represents the dynamic temperature of the medicament as the medicament is heated or cooled; wherein the temperature sensor is configured to communicate the detected temperature to the controller and to alert the controller when a preset temperature is reached; wherein the ready-to-use indicator is configured to alert a user when the preset temperature is reached, signifying the medicament is thermally ready to be delivered by the dispensing mechanism; and wherein the audio and/or visual indicator is configured to display one or more notifications to the user.

Embodiments may further provide a system wherein the injector may further comprise an initiator configured to interact with the controller to instruct the ready-to-use indicator to begin notification.

Embodiments may further provide a system wherein the initiator may be a battery isolator configured to isolate a battery from the injector.

Embodiments may further provide a system wherein the initiator may be a button.

Embodiments may further provide a system wherein the ready-to-use indicator may further comprise a pre-programmed timer; wherein the pre-programmed timer may be configured to count down from a predetermined time once an initiation signal has been received and to communicate a zero reading to the controller.

Embodiments may further provide a system wherein the temperature analog comprises one of more of a gas, liquid, or gel and the system further comprises a syringe configured to inject the one or more of the gas, liquid, or gel into the temperature analog through a body of the injector.

Embodiments may further provide a system wherein the temperature sensor may be further configured to detect an ambient temperature and communicate the ambient temperature to the controller.

Embodiments may further provide a system a system wherein the audio and/or visual indicator may further comprise one or more of an LED, a display, a speaker, or a vibration motor.

Embodiments may further provide a method of using an injector with a ready-to-use indicator, which may comprise activating a temperature sensor after the injector has been removed from a cold storage location; detecting the temperature of a temperature analog corresponding to the temperature of the medicament; and emitting a notification from the ready-to-use indicator that a preset temperature of the temperature analog has been reached, thus indicating that the medicament is also at the preset temperature and thermally ready for injection.

Embodiments may further provide a method that may further comprise filling the temperature analog with the one or more of the gas, liquid, or gel using a syringe.

Embodiments may further provide a method that may further comprise detecting an ambient temperature using a second temperature sensor; and setting the preset temperature as the ambient temperature.

Embodiments may further provide a method that may further comprise removing a battery isolator to activate the temperature sensor.

BRIEF DESCRIPTION OF THE DRAWINGS

Various aspects of the disclosure will now be described in connection with the attached drawings, in which.

DETAILED DESCRIPTION

In accordance with various aspects of the present disclosure, an injector with ready-to-use indicator may be a component for injection devices with refrigerated storage that may provide visual and/or audio indications to device users when a desired warm up time has been reached and the internal temperature of the device, and more specifically the injectable drug (medicament) which is to be administered, has reached an acceptable temperature for injection. The visual or audio indicators may be integrated into various types of injector systems and may be used in any form of injection device.

Figure 1:
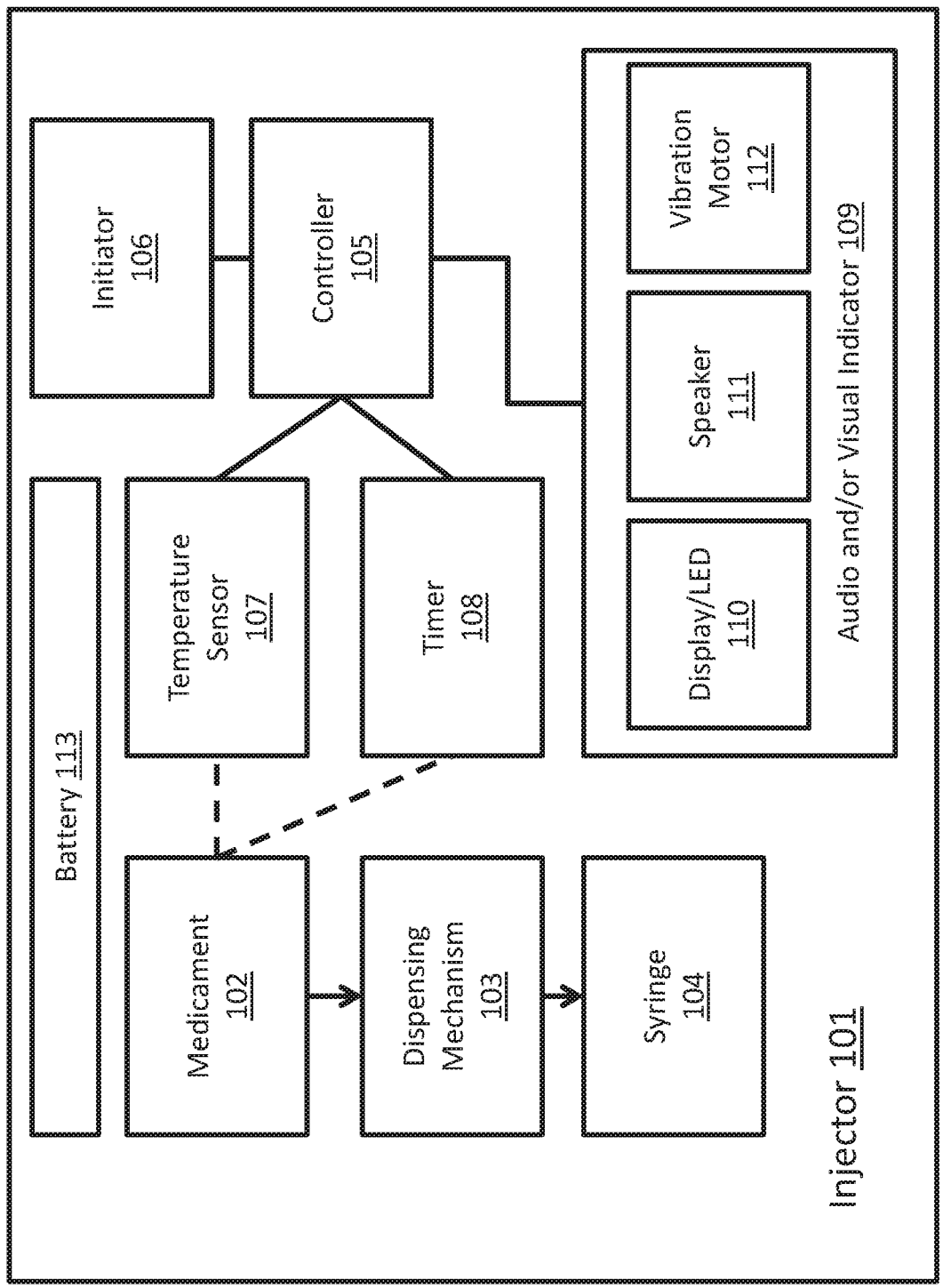
FIG. 1 is a block diagram illustrating the components of an injector with ready-to-use indicator, in accordance with various aspects of the present disclosure.

FIG. 1 is a block diagram illustrating the components of an injector with ready-to-use indicator, in accordance with various aspects of the present disclosure. The injector 101 may contain a measure of medicament 102, which is ultimately injected into a user via a syringe 104 and a dispensing mechanism 103, such as a plunger or automatic pressure dispenser. The medicament 102 may be temperature sensitive, and the entire injector 101 may be stored in cold storage prior to use to maintain medicament 102 viability. In one aspect, the injector 101 may be reusable, with the syringe 104 and medicament 102 being replaceable after use. According to another aspect, the injector 101 may be disposable.

Once the injector 101 is removed from cold storage, it may determine whether the medicament 102 is at a proper temperature to be delivered. In one aspect, a pre-programmed timer 108 may interact with a controller 105 in order to notify a user when the drug is ready for use (i.e., when the drug has reached acceptable temperature). The timer may be activated following removal of the device from cold storage through the activation of an initiator 106. The initiator 106 may include a battery isolator or a button, which may be incorporated into a light guide, and which may send the ready-to-use indicator an initiation signal.

The timer 108 may be pre-programmed based on the type of medicament 102 to be delivered. Once activated, the pre-programmed timer may start to count down until predetermined time for the drug to warm up has elapsed. The time duration necessary to warm up to the appropriate range of temperature may be determined based on the requirements of particular drugs or may be provided in standard intervals. For example, a thicker or more viscous medicament may require a longer duration out of cold storage before delivery, while a thinner or less viscous medicament may require a shorter time out of cold storage. In one aspect, the user may program the timer 108. In another aspect, the timer 108 may be preprogrammed by the manufacturer prior to sale or delivery.

The timer 108 may communicate with a central controller 105 in order to provide timing and/or alarm updates. The controller 105, in turn, may send commands to an audio and/or visual indicator 109 in order to provide notifications to the user regarding the medicament's 102 readiness. In one aspect, the notifications may be presented to the user through one or more of a combination of visual cues provided by a display and/or one or more LEDs 110, audio cues provided by a speaker 111, and/or tactile feedback provided by a vibration motor 112. A battery 113, timer 108, and audio and/or visual indicator 109 may be contained in the injector 101 through the use of a printed circuit board (PCB) or other circuit board.

Figure 2:
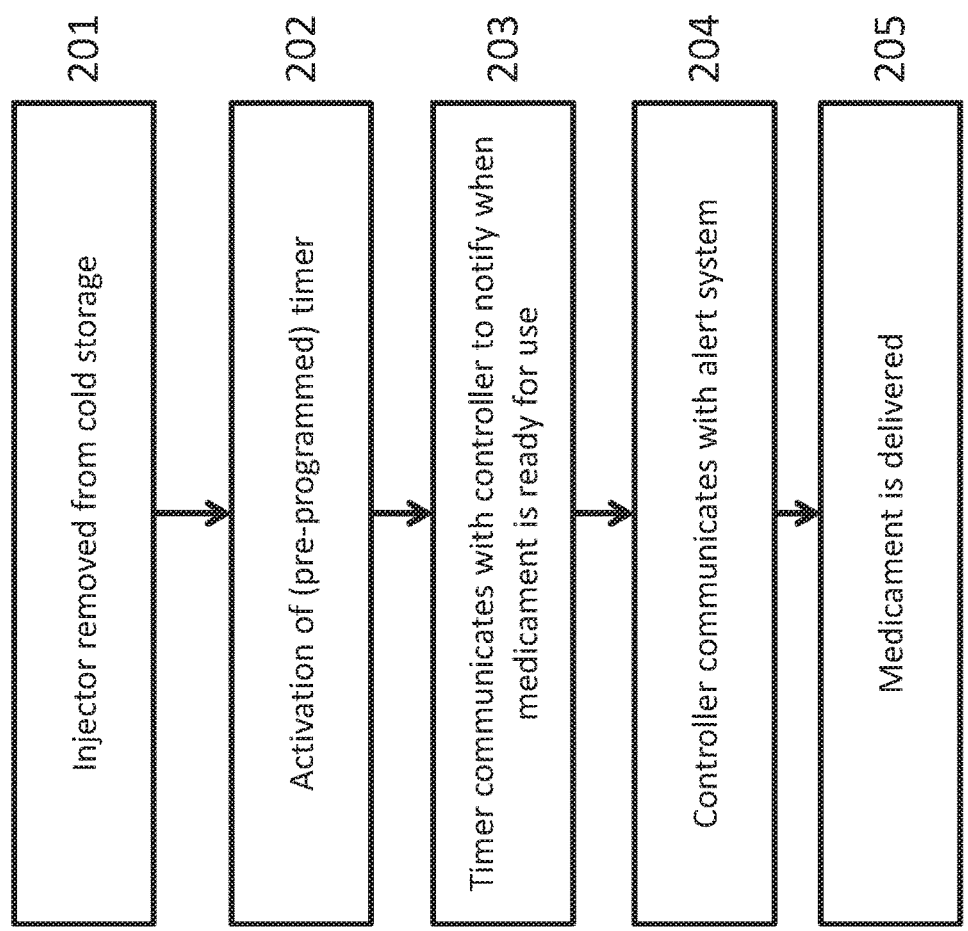
FIG. 2 depicts a flow diagram illustrating a method by which the injector with a ready-to-use indicator may be used, in accordance with various aspects of the present disclosure.

FIG. 2 depicts a flow diagram illustrating a method by which the injector with a ready-to-use indicator may be used, in accordance with various aspects of the present disclosure. The injector may be removed from cold storage 201. Next, the pre-programmed timer may be activated 202, e.g., through the use of an initiator tied to a controller. Next, the timer may communicate with the controller to notify when the countdown has completed and the medicament is ready for use 203. The controller may then communicate with the alert (audio and/or visual) system 204, and the user may deliver the medicament 205.

Returning to FIG. 1: According to a further aspect of this disclosure, a ready-to-use indicator may be a pre-programmed temperature sensor 107 that may notify the user when the medicament 102 is ready for use (i.e., when the medicament 102 reaches an acceptable use temperature) following removal of the injector 101 from the cold storage. In this aspect, a battery 112, temperature sensor/probe 107, and the audio and/or visual indicator 109 may be contained in the injector 101 through the use of a printed circuit board (PCB) or other circuit board.

The temperature sensor 107 may be activated following removal of the injector 101 from cold storage through the activation of the initiator 106. Once activated, the temperature sensor 107 may continuously monitor the temperature of the medicament and/or a temperature analog of the medicament until the temperature reaches the target temperature. In one aspect, the target temperature may be programmed by the user, or may be preprogrammed by the manufacturer prior to sale or delivery of the injector 107. In a further aspect, the temperature sensor 107 may also monitor the ambient temperature at the injector's 101 current location and may use the ambient temperature as the desired target temperature for the medicament.

Figure 3:
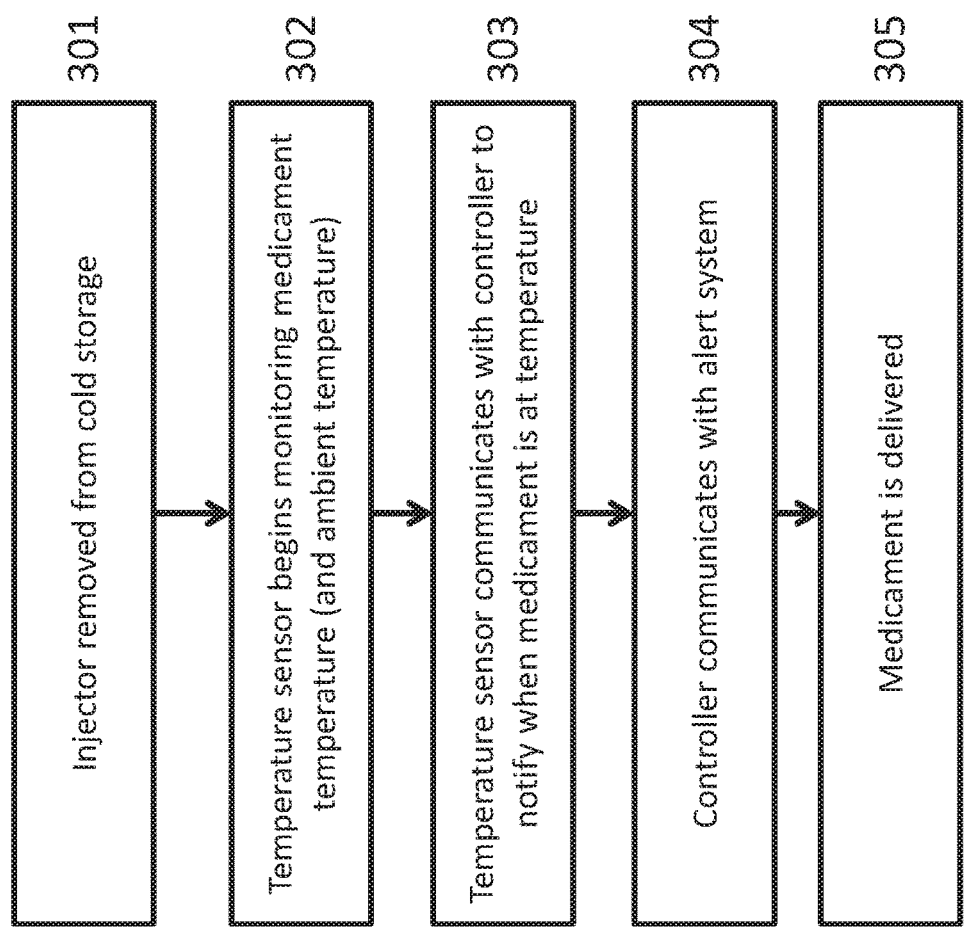
FIG. 3 depicts a flow diagram illustrating a method by which the injector with a ready-to-use indicator may be used, in accordance with various aspects of the present disclosure.

FIG. 3 depicts a flow diagram illustrating a method by which the injector with a ready-to-use indicator may be used, in accordance with various aspects of the present disclosure. The injector may be removed from cold storage 301. Next, the temperature sensor may be activated through the use of an initiator tied to a controller and may begin measuring the medicament temperature (and, in some cases, the ambient temperature) 302. Next, the temperature sensor may communicate with the controller to notify when the medicament is at the proper designated temperature and is ready for use 303. The controller may then communicate with the alert (audio and/or visual) system 304, and the user may then deliver the medicament 305.

Figure 4:
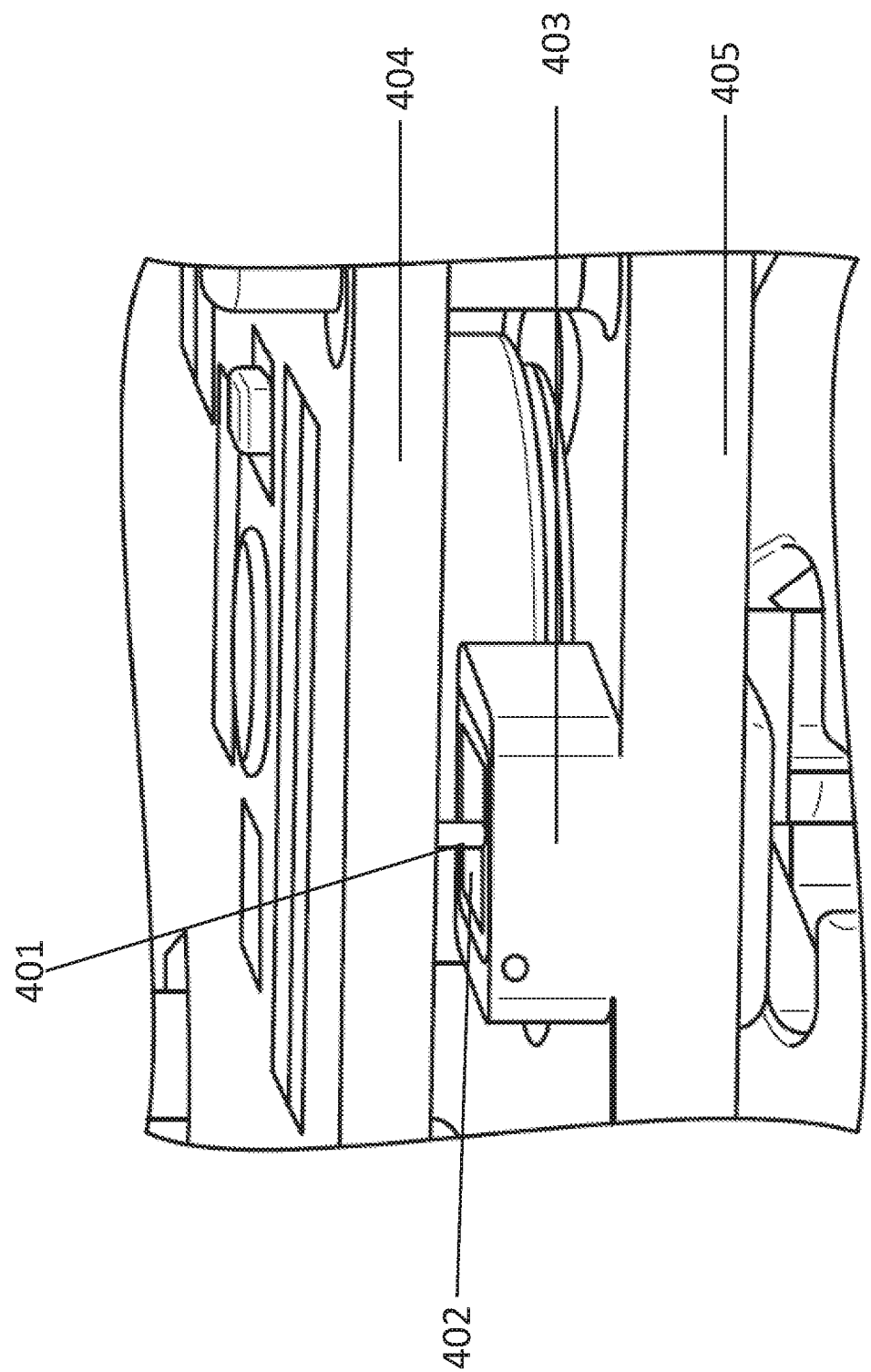
FIGS. 4 and 5 illustrate the placement of a temperature sensor and temperature analog within a ready-to-use indicator, in accordance with various aspects of the present disclosure.
Figure 5:
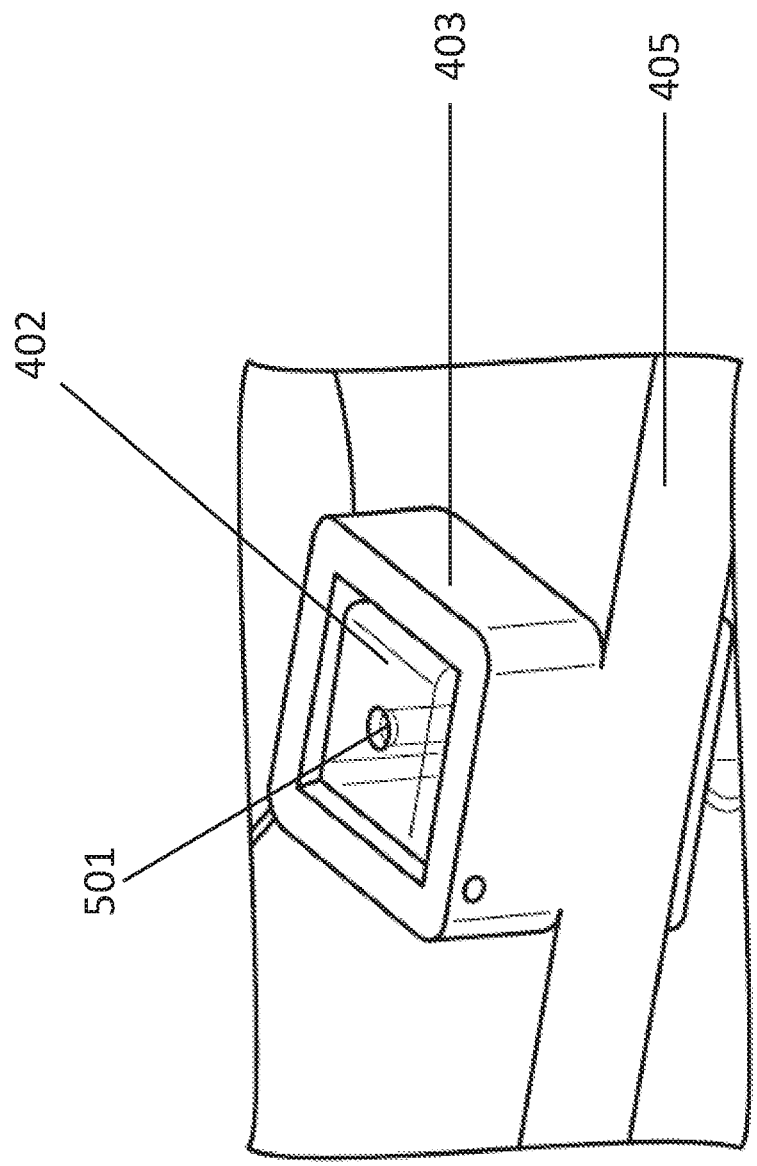

FIGS. 4 and 5 illustrate the placement of a temperature sensor and temperature analog within a ready-to-use indicator, in accordance with various aspects of the present disclosure. In one aspect, the temperature sensor 401 may be located in one or more strategic location(s) or may measure specific components to accurately represent the temperature of the given medicament. In another aspect, the temperature sensor 401 may be placed on the outer surface of the compartment holding the medicament. According to another aspect, the temperature sensor may be in contact with the medicament. Alternatively, a temperature analog 402 may be used to mimic the thermodynamics of the medicament, without requiring that the temperature sensor 401 be placed in close proximity to the medicament, such that measuring the temperature of the temperature analog 402 may provide the same or substantially the same temperature reading had the temperature of the medicament been measured directly instead. The temperature analog 402 may be a mass, either metallic or non-metallic, with similar thermodynamic properties to represent the medicament. For example, depending on the specific type and volume of the medicament, the temperature analog 402 may have the same time-dependent heat transfer properties of the medicament. For example, although a temperature analog 402 may displace a smaller volume inside the injector than the medicament, they may have the same or similar thermal conductivities and heat capacities. As such, measuring the temperature of the temperature analog 402 may provide a representation of the dynamic temperature of the medicament as both are heated or cooled. This may be accomplished, for example, by selecting an appropriately sized metallic mass and coating it with an insulating material. The temperature analog 402 with similar thermodynamic properties of the medicament may be placed in a temperature analog compartment 403 located near the temperature sensor 401. Either an insulating coating of the temperature analog 402, the temperature analog compartment 403, or both may simulate the heat transfer through the syringe material, such as, for example, a glass, polymer, or ceramic syringe. Therefore, the temperature analog 402 and the temperature analog compartment 403 may collectively have the same or substantially the same thermodynamic properties as the medicament and the syringe. As illustrated, the compartment 403 may be located on a PCB mounting board/plate 405, just below the PCB 404. The PCB 404 may contain the circuitry necessary for the functioning of the ready-to-use indicator, including the controller, LEDs, vibration motor, speaker, temperature sensor, timer circuit, etc. The temperature sensor 401 may be inserted into the temperature analog 402 through a sensor hole 501 to monitor the temperature change of the temperature analog 402, which thermodynamically represents the medicament. Thermodynamic representation may allow the temperature analog 402 to mimic the warming and cooling properties of the medicament. For example, if the medicament warms from freezing to room temperature in 20 minutes, the temperature analog 402 may also warm from freezing to room temperature in 20 minutes.

Figure 6:
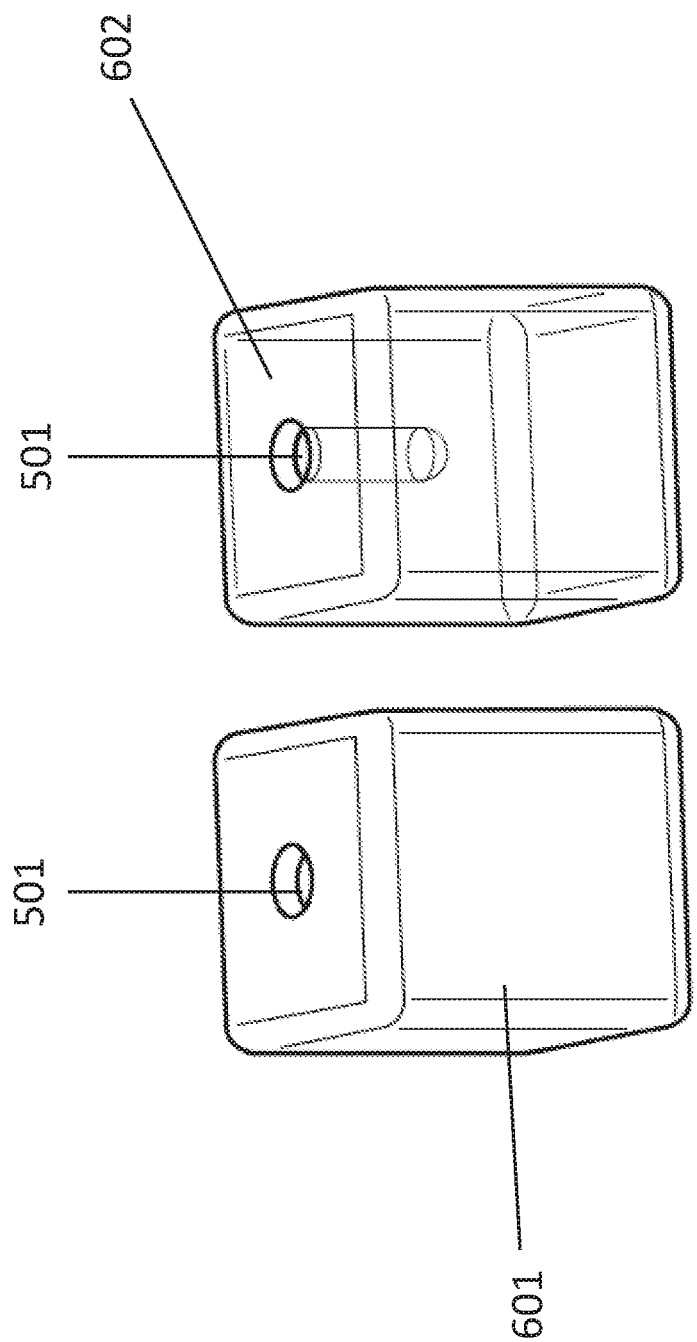
FIG. 6 illustrates various types of the temperature analog.
Figure 7:
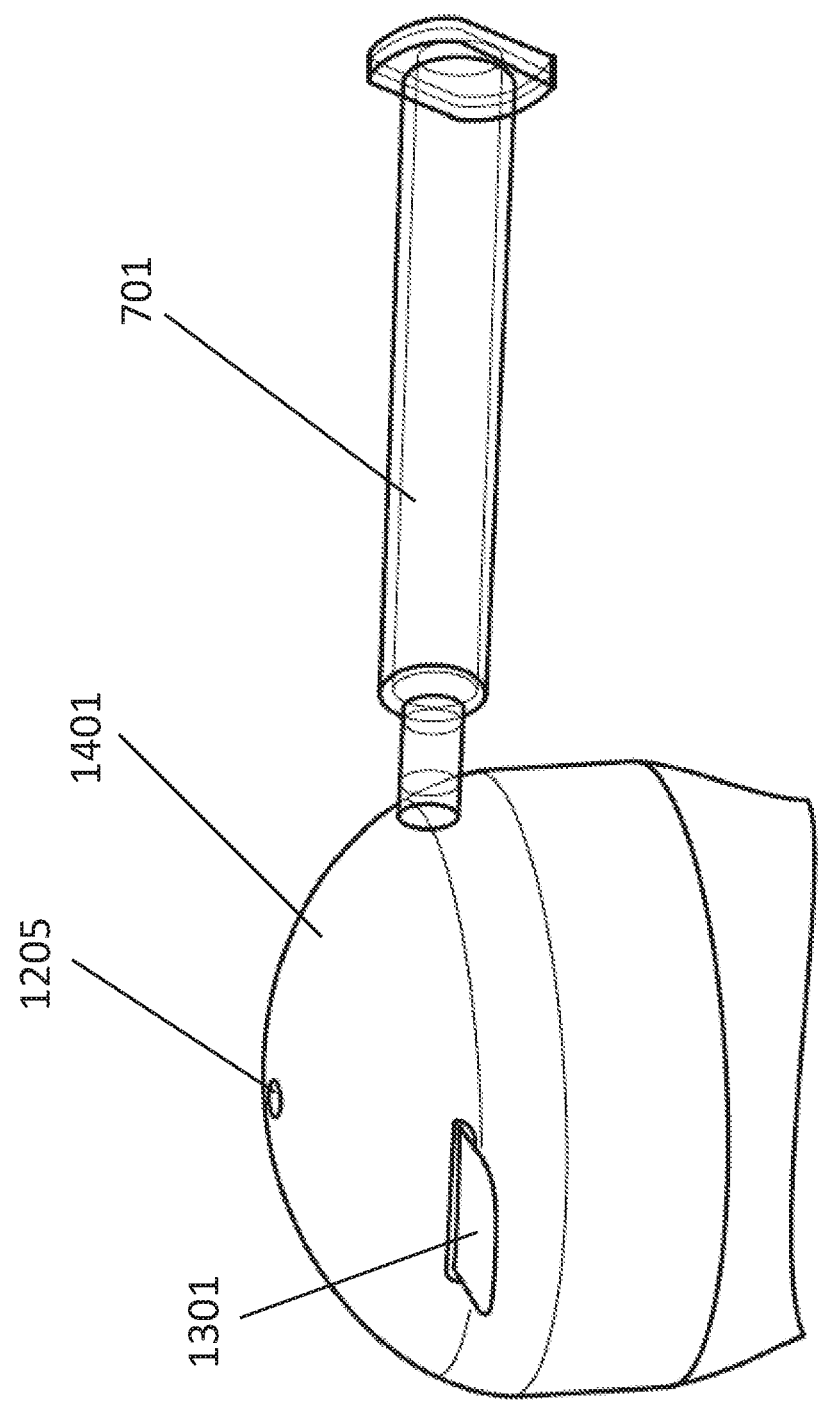
FIG. 7 illustrates the filling of the temperature analog.

FIG. 6 illustrates various aspects of the temperature analog. The temperature analog used for monitoring may be metal 601, non-metal, gel, liquid or gas. For gel, liquid, and gas temperature analogs 602, the temperature analog may be an elastomeric sealed container enclosing the temperature sensor which may be filled via a syringe (FIG. 7, 701). The syringe 701 shown in FIG. 7 may be of any size appropriate for the volume of the filling material. Filling may be performed during manufacture, or before the injector is placed into cold storage.

In another embodiment not shown, the temperature analog 402 may be directly mounted to the PCB 404. In such a case, the temperature sensor 401 may be mounted in between the temperature analog 402 and the PCB 404, or the temperature sensor 401 may be potted inside a cavity of the temperature analog 402. In further embodiments, the temperature analog 402 may be comprised of dissimilar metals, such as to have thermal electric properties of a thermal couple. In such a case, the temperature analog 402 would itself operate as a temperature sensor. Optionally, a second temperature sensor (not shown) may be used to measure the ambient temperature of the surroundings. The controller may optionally use the ambient temperature to help determine a temperature at which the medicament is to be dispensed.

Figure 8:
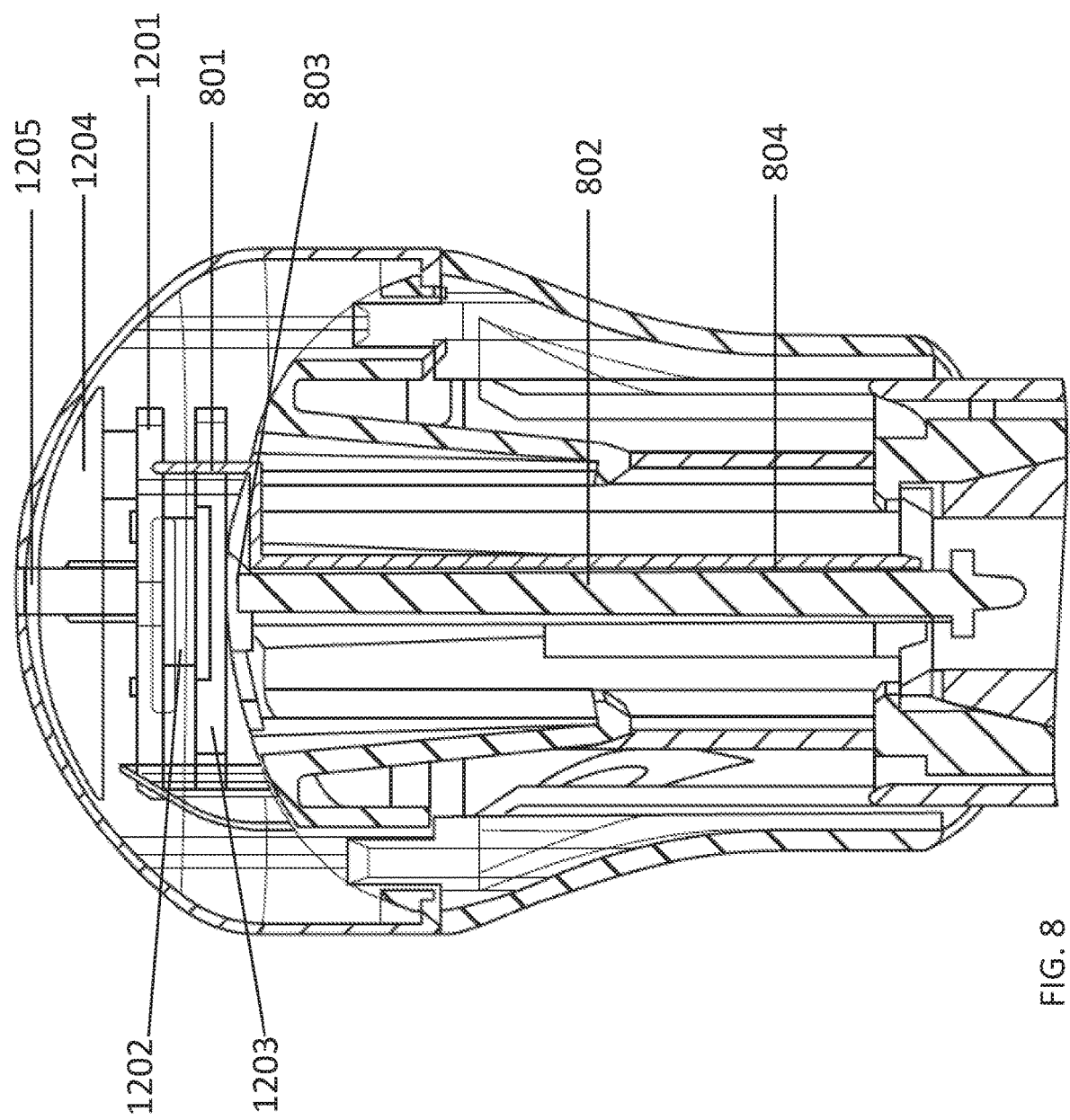
FIGS. 8 and 9 illustrate cross-section views showing the placement of a temperature sensor within an injector, in accordance with various aspects of the present disclosure.
Figure 9:
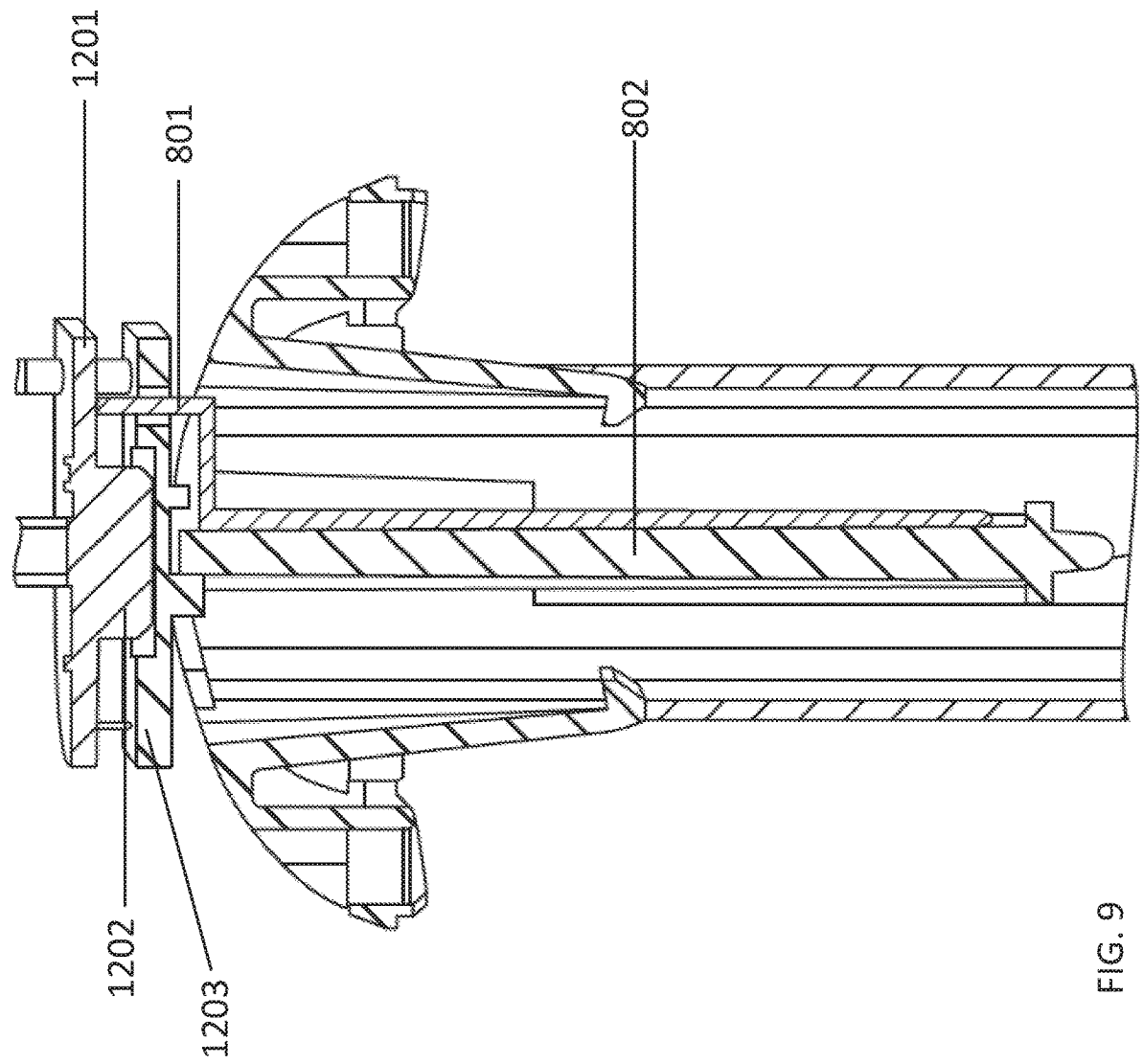

FIGS. 8 and 9 illustrate the placement of a temperature sensor within an injector, in accordance with various aspects of the present disclosure. If the measurement of a temperature analog is not possible, due to lack of space availability or for any other reason, the temperature sensor 801 may be strategically located to come in contact with the syringe 802 filled with medicament. In one aspect, the temperature sensor 801 may measure the ambient temperature above a stopper 803 within the filled syringe (medicament syringe) 802 or the temperature of the syringe wall 804.

Figure 10:
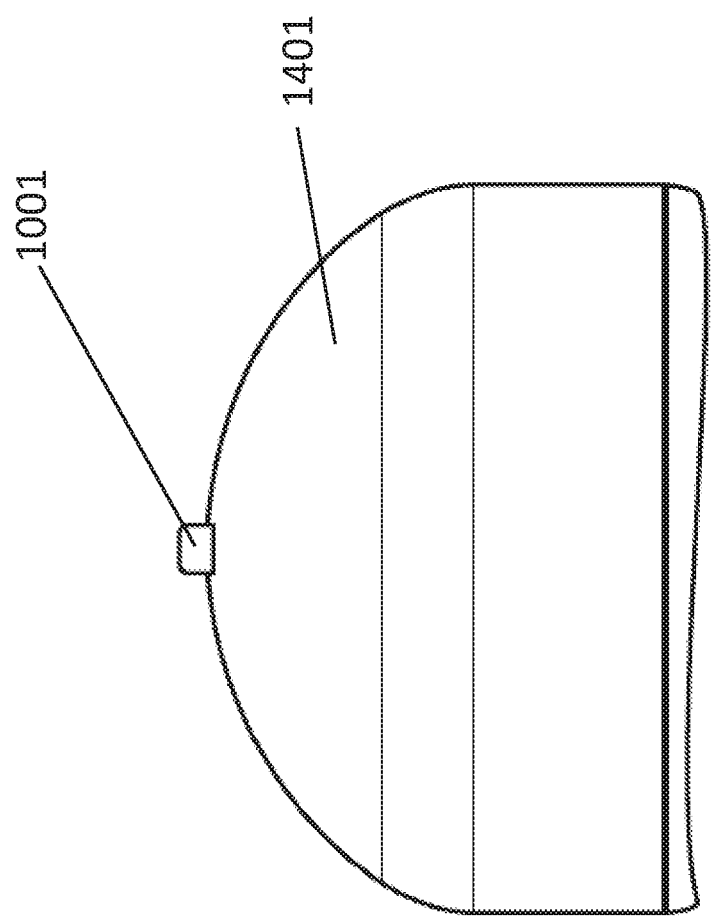
FIGS. 10 and 11 illustrate various aspects of the audio and/or visual indicator used in the ready-to-use-indicator.
Figure 11:
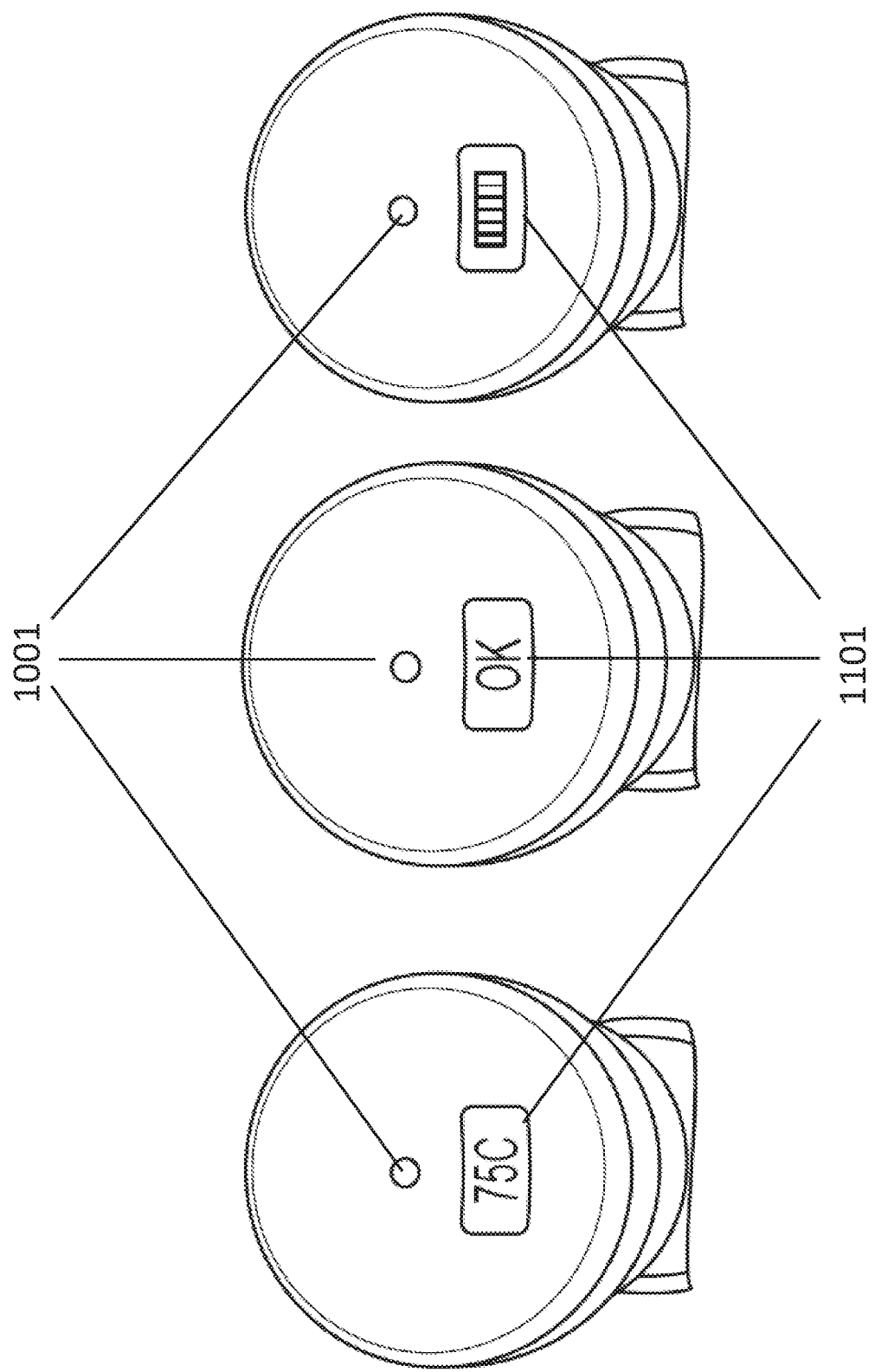

FIGS. 10 and 11 illustrate various examples of the audio and/or visual indicator used in the ready-to-use-indicator. At either the pre-programmed time or after reaching a pre-set temperature, one or more of LEDs 1001, display 1101, speaker, and vibration motor may be activated to indicate to the user that the device is ready to use. During notification of the ready-to-use condition, the display 1001, speaker, and vibration motor may be utilized to alert the user of the status of the medicament and its readiness. In examples using LEDs 1001, different colors and/or blinking patterns may be used to indicate different states. For example, blinking blue may indicate that the device is warming up, while solid green may indicate ready for use. In another example, a solid red may indicate "do not use, device is not ready," whereas solid green may indicate "ready for use". In examples using an LCD screen 1101, either numerical, verbal, or graphical indication(s) may be shown to let the user know when they may use the device.

Figure 12:
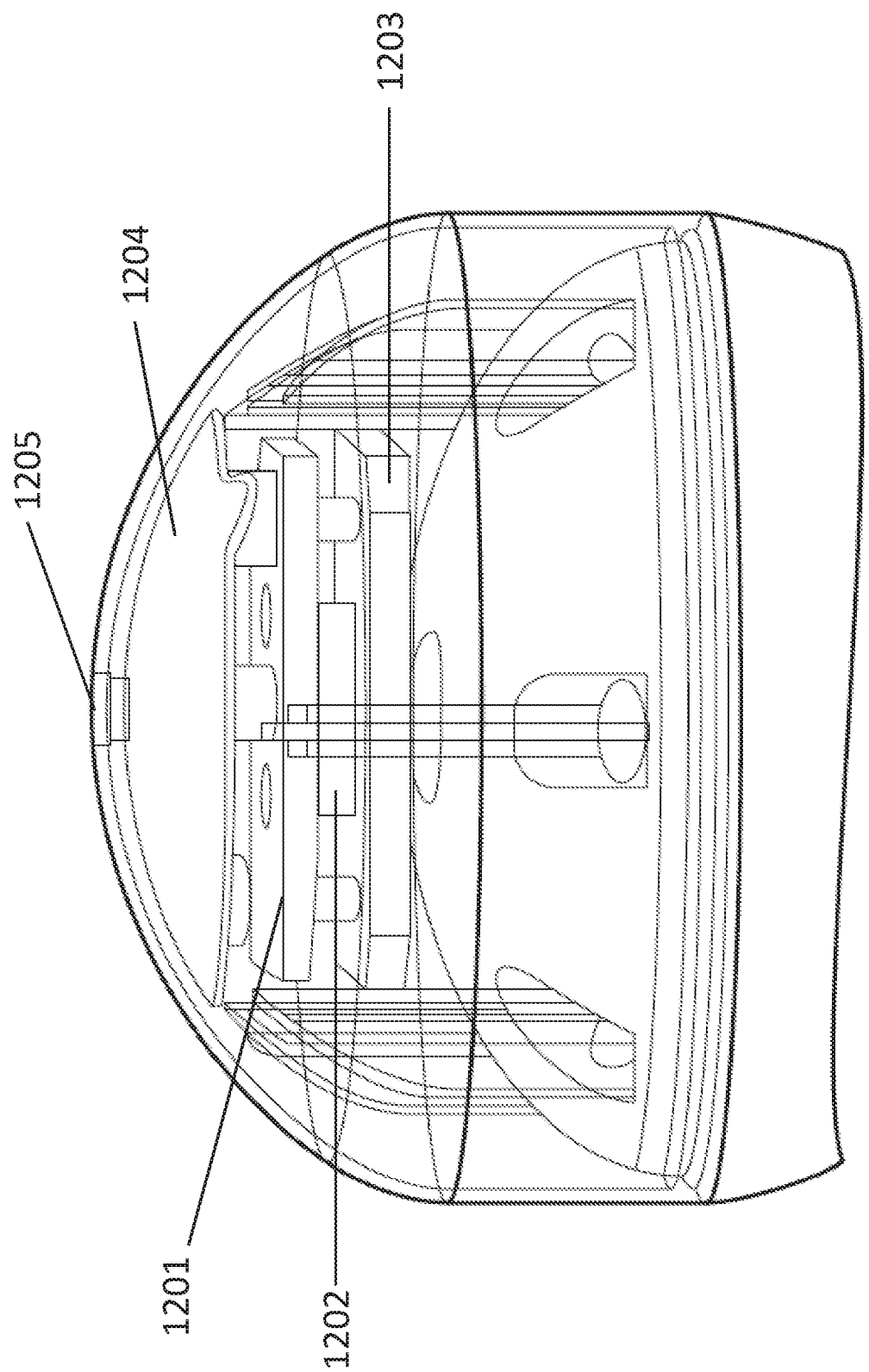
FIG. 12 illustrates a cut-away view of an injector with ready-to-use indicator, in accordance with various aspects of the present disclosure.

FIG. 12 illustrates a cut-away view of an injector with ready-to-use indicator, in accordance with various aspects of the present disclosure. The components of the audio and/or visual indicator may include a printed circuit board (PCB) assembly 1201 with a processor, LEDs, a speaker, timer, temperature sensor 1202, a light guide 1205, a PCB mounting board/plate 1203, and/or a battery 1204. The light guide 1205 may act as an optical conduit such that the LEDs on the PCB 1201 are more visible to the user. The light guide 1205 may also be depressible, and may act as the initiator.

Figure 13:
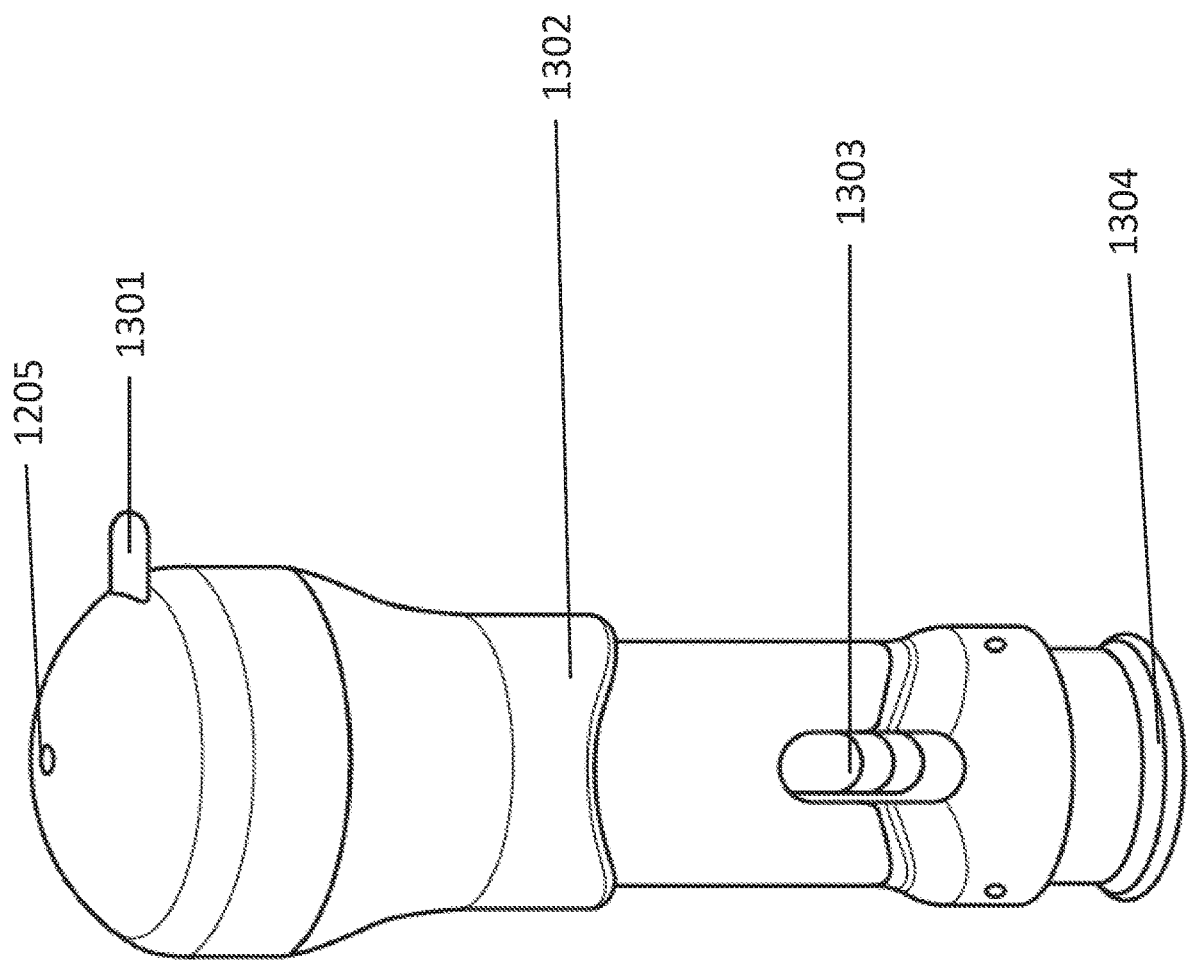
FIGS. 13-15 illustrate various form factors for an injector with ready-to-use indicator, in accordance with various aspects of the present disclosure.
Figure 14:
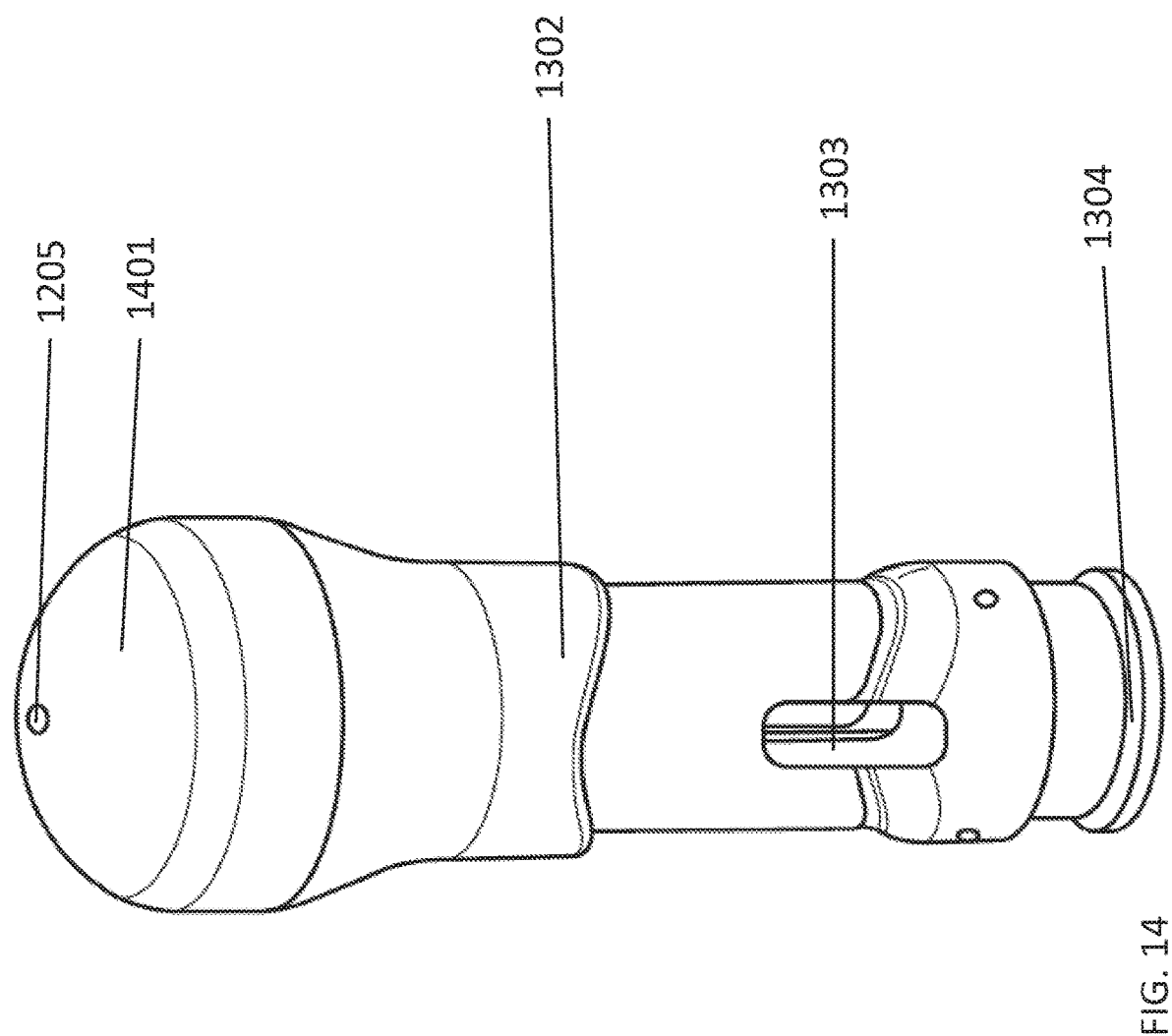
Figure 15:
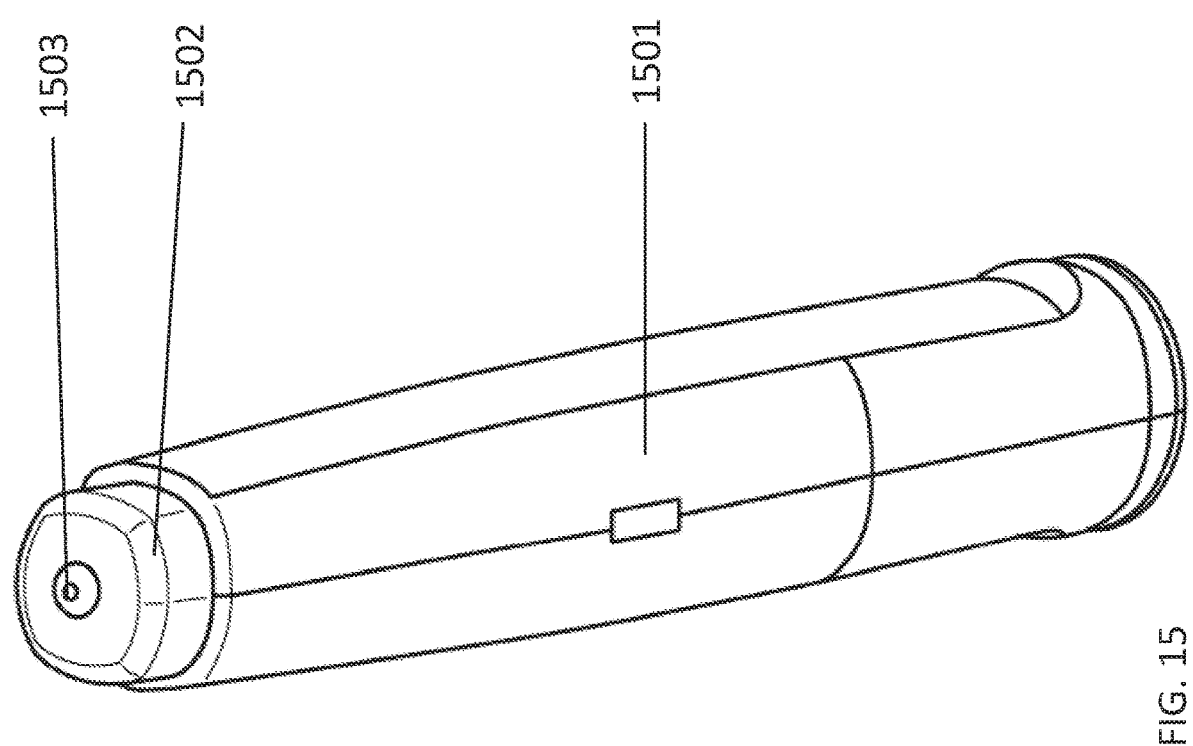

FIGS. 13-15 illustrate various form factors for an injector with ready-to-use indicator, in accordance with various aspects of the present disclosure. In FIG. 13, the injector may have a body 1302, which may be cylindrical in overall shape. The body 1302 may have a viewing port 1303, which may be used by the user to view the vial of medicament. Additionally, the body 1302 may have a dispensing end 1304, which may act as a safety sheath to hide the hypodermic needle through which the medicament is applied. The light guide 1205, which may amplify the light signal of the LED, may be disposed on the top of the body 1302. A pull-tab 1301 may be used as the initiator, in that the pull tab may be used to isolate the battery from providing power prior to the pull tab 1301 being removed. Alternatively, as shown in FIG. 14, the injector may use the light guide 1205 as a button and an initiator, such that the ready-to-use indicator will not activate until depressed. The injector may have a top cap 1401 with or without a slot for a pull tab. FIG. 15 illustrates a different form factor for the injector, with a solid body 1501 without viewing port, and a depressible injection button 1502 disposed on the top of the body. The button 1502 may be topped with a light guide 1503.

These aspects are not meant to be limiting. For different injector systems, the positioning and size of the circuit may vary. It will be appreciated by persons skilled in the art that the present disclosure is not limited by what has been particularly shown and described hereinabove. Rather the scope of the present disclosure includes both combinations and sub-combinations of various features described hereinabove as well as modifications and variations which would occur to persons skilled in the art upon reading the foregoing description and which are not in the prior art.

What is claimed is:

1. An injection system, comprising:
   an injector further comprising:
   a dispensing mechanism configured to dispense a medicament;
   a ready-to-use indicator further comprising:
   a controller configured to interact with the ready-to-use indicator and an audio and/or visual indicator;
   a temperature sensor; and a temperature analog having similar thermodynamic properties to the medicament;

wherein the temperature sensor is configured to detect a temperature of the temperature analog which represents a dynamic temperature of the medicament as the medicament is heated or cooled;

wherein the temperature sensor is configured to communicate the detected temperature to the controller and to alert the controller when a preset temperature is reached;

wherein the ready-to-use indicator is configured to alert a user when the preset temperature is reached, signifying the medicament is thermally ready to be delivered by the dispensing mechanism; and wherein the audio and/or visual indicator is configured to indicate one or more notifications to the user.

2. The system as recited in claim 1, wherein the injector further comprises: an initiator configured to interact with the controller to instruct the ready-to-use indicator to begin notification.

3. The system as recited in claim 2, wherein the initiator is a battery isolator configured to isolate a battery from the injector.

4. The system as recited in claim 2, wherein the initiator is a button.

5. The system as recited in claim 1, wherein the ready-to-use indicator further comprises:

a pre-programmed timer;

wherein the pre-programmed timer is configured to count down from a predetermined time once an initiation signal has been received and to communicate a zero reading to the controller.

6. The system as recited in claim 1, wherein the temperature analog comprises one of more of a gas, liquid, or gel; and the system further comprises a syringe configured to inject the one or more of the gas, liquid, or gel into the temperature analog through a body of the injector.

7. The system as recited in claim 1, wherein the temperature sensor is further configured to detect an ambient temperature and communicate the ambient temperature to the controller.

8. The system as recited in claim 1, wherein the audio and/or visual indicator further comprises:

one or more of an LED, a display, a speaker, or a vibration motor.

9. The system of claim 1, wherein the temperature analog is a liquid or gel.

10. The system of claim 1, wherein the temperature analog is a metallic or non-metallic mass.

11. The system of claim 10, wherein the temperature analog is coated with an insulating material.

12. The system of claim 1, further comprising:

a temperature analog compartment configured to contain an entirety of the temperature analog.

13. The system of claim 12, wherein the temperature analog compartment is located near the temperature sensor.

14. The system of claim 12, wherein the temperature analog compartment defines a sensor hole, and the temperature sensor is configured to extend through the sensor hole so as to come into contact with the temperature analog.

15. A method of using an injector with a dispensing mechanism configured to dispense a medicament and a ready-to-use indicator, comprising:

activating a temperature sensor after the injector has been removed from a cold storage location;

detecting a temperature of a temperature analog corresponding to a temperature of the medicament, wherein the temperature analog has similar thermodynamic properties to the medicament; and emitting a notification from the ready-to-use indicator that a preset temperature of the temperature analog has been reached, thus indicating that the medicament is also at the preset temperature and thermally ready for injection.

16. The method as recited in claim 15, further comprising: filling the temperature analog with the one or more of a gas, liquid, or gel using a syringe.

17. The method as recited in claim 15, further comprising: detecting an ambient temperature using a second temperature sensor; and setting the preset temperature as the ambient temperature.

18. The method as recited in claim 15, further comprising: removing a battery isolator to activate the temperature sensor.

* * * * *